United States Patent
Rasmussen et al.

(10) Patent No.: US 7,057,014 B2
(45) Date of Patent: Jun. 6, 2006

(54) PEPTIDE PURIFICATION

(75) Inventors: Jon H. Rasmussen, Lyngby (DK); Palle H. Rasmussen, Bagsværd (DK)

(73) Assignee: Polypeptide Laboratories A/S (DK)

( * ) Notice: Subject to any disclaimer, the term of this patent is extended or adjusted under 35 U.S.C. 154(b) by 0 days.

(21) Appl. No.: 10/500,302

(22) PCT Filed: Dec. 23, 2002

(86) PCT No.: PCT/IB02/05581

§ 371 (c)(1),
(2), (4) Date: Jan. 12, 2005

(87) PCT Pub. No.: WO03/055900

PCT Pub. Date: Jul. 10, 2003

(65) Prior Publication Data

US 2006/0014694 A1    Jan. 19, 2006

(30) Foreign Application Priority Data

Dec. 29, 2001 (SE) .................................. 0104462

(51) Int. Cl.
*A61K 38/08* (2006.01)

(52) U.S. Cl. .......................................... 530/328; 514/2

(58) Field of Classification Search ..................... None
See application file for complete search history.

(56) References Cited

FOREIGN PATENT DOCUMENTS

| EP | 0 136 728 | | 4/1985 |
|---|---|---|---|
| WO | WO-00/18423 | | 4/2000 |
| WO | WO 00/18423 | * | 6/2000 |

OTHER PUBLICATIONS

Sakamoto, et al., Journal of Antibiotics, 1993, 46, 1788-1798.*

* cited by examiner

*Primary Examiner*—Bruce R. Campell
*Assistant Examiner*—Satyanarayana R. Gudibande
(74) *Attorney, Agent, or Firm*—Dickstein, Shapiro, Morin & Oshinsky, LLP.

(57) ABSTRACT

A nona- or decapeptide is purified from residual organic solvent by dissolving in a solvent comprising water and at least one $C_1$–$C_3$ alcohol followed by precipitation into a vigorously stirred solvent consisting of an alkyl ester of a carboxylic acid, the ester comprising from 3 to 6 carbon atoms, and one or several non-polar compounds selected from hexane, heptane, octane, cyclohexane, methylcyclohexane, and, optionally, of up to 5% of acetic or propionic acid, isolating the precipitated nona- or decapeptide, followed by washing with a mixture of $C_3$–$C_5$ esters and drying, with the provisio that the water content of the solvent comprising water and the at least one alcohol is below 8% (v/v), and that the volume ratio of the dissolution solvent mixture and the precipitation solvent mixture is 1:10 or higher. Also described is the monoacetate of Ac-D-2Nal-D-4ClPhe-D-3Pal-Ser-MeTyr-D-Asn-Leu-Lys(iPr)-Pro-D-Ala-$NH_2$.

9 Claims, No Drawings

PEPTIDE PURIFICATION

FIELD OF THE INVENTION

The present invention relates to the purification of peptides, in particular intermediate-size peptides, more particularly nona- and decapeptides, such as LHRH-antagonists.

BACKGROUND OF THE INVENTION

Most intermediate size natural and synthetic peptides are amorphous substances. Many of them have pharmacologically interesting properties, such as many nona- and decapeptides which are LHRH (luteinizing hormone-releasing hormone) antagonists. One particular substance of this kind known only in amorphous form is the synthetic decapeptide of the formula (I)

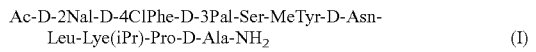

(I)

which, being a potent LHRH antagonist, has desirable pharmacological properties.

For use in pharmaceutical preparations it is necessary for the LHRH antagonist (I) and nona- and decapeptides of similar structure to be essentially pure. The raw product obtained in the last step of a multiple-step synthesis is purified by chromatographic and other methods. To eliminate residual solvent from the chromatography a thus purified product usually has to be dissolved in an aqueous medium and freeze-dried. This is a costly process producing a voluminous product which is not easy to handle.

A process of purification of an otherwise pure peptide from residual organic solvent by other means than freeze-drying thus is desirable.

WO 0018423 A discloses the use of the combination of cyclodextrin and a LHBR peptide analogue, including its pharmaceutically acceptable salts, for the preparation of a pharmaceutical composition for oral administration. Abarelix is a preferred LHRM analogue. Acetate salts of the LHRH peptide antagoniste of D1 are disclosed to be pharmaceutically acceptable in general. The compounds of WO 0018423 are useful in the manufacture of medicaments.

WO 0055190 A discloses decapeptide LHRM antagonists for the manufacture of medicaments against hormone dependent tumors and hormone influenced diseases, which may be purified by preparative HPLC, and freeze dried.

EP 0955308 A discloses a process for the transformation or hydrochloride salts of decapeptide LHRH antagonists to their diacetate salts in a concurrent single-step purification by liquid chromatography.

OBJECTS OF THE INVENTION

It is an object of the present invention to provide a process of purification of an otherwise pure peptide of the aforementioned kind from residual organic solvent, which avoids freeze-drying.

It is another object of the present invention to provide such an otherwise pure peptide, which is essentially free from residual organic solvent and is not in the form of a cryoprecipitate.

Further objects of the invention will become obvious from the following summary of the invention, the description of a preferred embodiment thereof, And the appended claims.

SUMMARY OF THE INVENTION

According to the present invention is provided a process of purification of an otherwise pure peptide, in particular a nona- or decapeptide, most particularly a nona- or decapeptide which is an LHRH antagonist, from residual organic solvent, comprising the following steps:
  dissolving said otherwise pure peptide in a dissolution solvent mixture comprising water and at least one alcohol selected from methanol, ethanol, propanol, isopropanol;
  adding the solution of the otherwise pure peptide in said solvent mixture to a vigorously stirred precipitation solvent mixture essentially consisting of one or several polar compounds selected from methyl acetate, ethyl acetate, methyl propionate, isopropionate, butyl acetate, isobutyl acetate, t-butyl acetate, ethyl formate, propyl formate, isopropyl formate, and one or several non-polar compounds selected from hexane, heptane, octane, cyclohexane, methylcyclohexane, and, optionally, of up to 5% of acetic or propionic acid;
  isolating the precipitated peptide;
  washing the isolated peptide with one or a mixture of said polar compounds or a solvent or solvent mixture of said polarity,
  drying the washed peptide, with the proviso that the water content of said solvent mixture comprising water and at least one alcohol is below 8% (v/v), and that the volume ratio of the dissolution solvent mixture and the precipitation solvent mixture is 1:10 or more.

"An otherwise pure peptide" is a peptide which is sufficiently pure for use in a medicine except for volatile impurities which need to be removed or the content of which needs to be substantially reduced. The otherwise pure peptide will normally be a substance having undergone purification by chromatography.

Preferably the otherwise pure peptide is

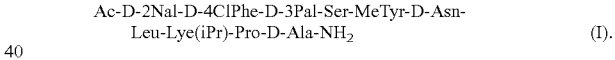

(I).

According to a first preferred aspect of the invention the water content of the dissolution solvent mixture is below 5% (v/v).

According to a second preferred aspect of the invention the volume ratio of the dissolution solvent mixture and the Precipitation solvent mixture is at least 1:15, in particular at least 1:20.

According to a third preferred aspect of the invention the alcohol of the dissolution solvent mixture is ethanol.

According to a fourth preferred aspect of the invention the polar component of the precipitation solvent mixture is ethyl acetate.

According to a fifth preferred aspect of the invention the non-polar component of the precipitation solvent mixture is heptane.

In the following the invention will be described in greater detail by reference to a preferred embodiment thereof which should not be understood to limit the invention.

DESCRIPTION OF A PREFERRED EMBODIMENT

EXAMPLE 1

The fractions containing pure compound (1) (100 g in total) in ethanol-water-acetic acid 40:59:1 (v/v/v) obtained from preparative HPLC by which the synthetically obtained product had been purified were pooled and concentrated in vacuo to an oil which was co-evaporated twice from ethanol. The resulting solid was dissolved in 440 ml of ethanol and the resulting clear solution added over a period of 20 min to 8.8 L of ethyl acetate/heptane 1:1 (v/v).

Stirring was continued for 1 hour and filtered. The amorphous product was washed with 3 L of ethyl acetate; it was found that this removed nearly all heptane. The washed product was dried in a vacuum oven at 40° C. at 0.3 bar for 48 hrs. Elemental analysis of the dried product indicated that the monoacetate of (I) had be obtained. Cryoprecipitation, in contrast, produces the corresponding diacetate. In the following Table analytical parameters of the monoacetate of (I) produced according to the invention are compared with those of a corresponding lyophilized product (diacetate).

TABLE

All percentages are by weight

|  | lyophilized product | precipitated product |
|---|---|---|
| Water | 3.4% | 3.0% |
| Ethanol | <0.024% | <0.024% |
| Ethyl acetate | <0.024% | <0.024% |
| Heptane | <0.024% | <0.024% |
| Acetic acid (as acetate) | 7.5% | 3.9% |
| HPLC purity | 99.8% | 99.8% |
| Peptide content | 88.8% | 94.9% |
| Loss in filtrate | — | 0.3% |

EXAMPLE 2

Variation of the composition of the precipitation solvent or solvent mixture: otherwise, procedure as in Example 1. Precipitation in pure ethyl acetate results in from about 3% to about 5% by weight loss of peptide. Precipitation in pure heptane results in a sticky product which is difficult to filter. A 1:1 (v/v) mixture of ethyl-acetate hexane lives a product which is easy to filter and dry; in repeated experiments the loss of peptide was always leas than 0.5% by weight.

EXAMPLE 3 variation of water content of the solution of oily product in the dissolution solvent (absolute ethanol), otherwise, procedure as in Example 1. A water content of 10% (v/v) results in a sticky product on precipitation which is difficult to filter. A water content of 15% (v/v) results in an oily product on precipitation. To obtain satisfactory result the water content must not exceed 8% (v/v) but should preferably be kept below 5% (v/v). A water content below 5% is accomplished by co-evaporating the oily product from the chromatography at least twice with ethanol.

EXAMPLE 4

Variation in precipitation temperature: otherwise, procedure as in Example 1. The precipitation temperature proved to be not critical. It could be varied from 0° C. to 20° C. without noticeable differences in product yield and morphology.

EXAMPLE 5

Variation of concentration of (I) in the dissolution solvent; otherwise, procedure as in Example 1. It was found that the concentration of the oily product from the chromatography which had been co-evaporated with ethanol in the dissolution solvent should be as high as possible. Even a concentration of 330 g by weight could be used.

EXAMPLE 6

Variation of ratio between dissolution solvent and precipitation solvent volumes and other variations otherwise, procedure as in Example 1. The optimum ratio was found to be about 1:20. It could be shown that ratios from 1:15 to 1:30 gave satisfactory results. A ratio of 1:10 resulted in a sticky product. Precipitation is very fast. The suspension can be filtered 30 min after the last addition of dissolved substance. Washing with ethyl acetate did not result in loss of product but efficiently removed heptane.

The invention claimed is:

1. A process of removing residual organic solvent from an otherwise pure nona- or decapeptide, comprising the following steps:
   dissolving the nona- or decapeptide in a dissolution solvent mixture comprising water and at least one alcohol selected from a group consisting of methanol, ethanol, propanol, isopropanol;
   adding the solution of the nona- or decapeptide in said solvent mixture to a vigorously stirred precipitation solvent mixture consisting essentially of one or several polar compounds selected from a group consisting of methyl acetate, ethyl acetate, methyl propionate, ethyl propionate, butyl acetate, isobutyl acetate, t-butyl acetate, ethyl formate, propyl formate and isopropyl formate, and one or several non-polar compounds selected from a group consisting of hexane, heptane, octane, cyclohexane and methylcyclohexane, and, optionally of up to 5% of acetic or propionic acid;
   isolating the precipitated nona- or decapeptide;
   washing the isolated nona- or decapeptide with one or a mixture of said polar compounds or a solvent or solvent mixture of similar polarity,
   drying the washed nona- or decapeptide,
   with the proviso that the water content of said solvent mixture comprising water and at least one alcohol is below 8% (v/v), and that the volume ratio of the dissolution solvent mixture and the precipitation solvent mixture is 1:10 or more.

2. The process of claim 1, wherein the water content of said solvent mixture comprising water and at least one alcohol is below 5% (v/v).

3. The process of claim 1, wherein said nona- or decapeptide is an LHRH antagonist.

4. The process of claim 3, wherein said nona- or decapeptide is Ac-D-2Nal-D-4ClPhe-D-3Pal-Ser-MeTyr-D-Asn-Leu-Lys(iPr)-Pro-D-Ala-$NH_2$ (I).

5. The process of claim 4, wherein Ac-D-2Nal-D-4ClPhe-D-3Pal-Ser-MeTyr-D-Asn-Leu-Lys(iPr)-Pro-D-Ala-$NH_2$ (I) is obtained in form of the monoacetate.

6. The process of claim 1, wherein the volume ratio of the dissolution solvent mixture and the precipitation solvent mixture is at least 1:15.

7. The process of claim 1, wherein the alcohol of the dissolution solvent mixture is ethanol.

8. The process of claim 1, wherein the polar component of the precipitation solvent mixture is ethyl acetate.

9. The process of claim 1, wherein the non-polar component of the precipitation solvent mixture is heptane.

* * * * *